US006129921A

United States Patent [19]

Hooper et al.

[11] Patent Number: 6,129,921

[45] Date of Patent: *Oct. 10, 2000

[54] VIRAL RIBONUCLEOCAPSID AS AN IMMUNOLOGICAL ENHANCER

[75] Inventors: Douglas Craig Hooper, Medford, N.J.; Bernhard Dietzschold, Newtown Square; Hilary Koprowski, Wynnewood, both of Pa.

[73] Assignee: Thomas Jefferson University, Philadelphia, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/567,713

[22] Filed: Dec. 5, 1995

Related U.S. Application Data

[63] Continuation of application No. 08/230,158, Apr. 19, 1994, abandoned.

[51] Int. Cl.[7] ........................ A61K 39/29; A61K 39/205; A61K 47/00; C07K 14/00

[52] U.S. Cl. .................................... 424/224.1; 424/130.1; 424/184.1; 424/187.1; 424/193.1; 424/196.11; 424/204.1; 424/278.1; 530/403; 530/806; 530/826

[58] Field of Search ............................. 424/184.1, 187.1, 424/193.1, 196.11, 204.1, 224.1, 130.1, 278.1; 530/403, 806, 826

[56] References Cited

U.S. PATENT DOCUMENTS 4,320,115 3/1982 Bijlenga et al. .......................... 424/84

FOREIGN PATENT DOCUMENTS

WO 8900861 2/1989 WIPO .

OTHER PUBLICATIONS

Fu, Z.F., et al., "Rabies virus nucleoprotein expressed in and purified from insect cells is efficacious as a vaccine", *Proc. Natl. Acad. Sci. USA* (1991) 88:2001–2005.

Schneider et al., "Rabies Group–Specific Ribonucleo–protein Antigen and a Test System for Grouping and Typing of Rhabdoviruses", *J. Virol.* (1973) 11:748–755.

Wiktor, T.J., et al., "Induction and Biological Properties of Defective Interfering Particles of Rabies Virus", *J. Virol.* (1977) 21 626–635.

Erickson, B.W. and Merrifield, R.B. (1976) In: Neurath, H., Hill, R.L. (eds) *The Proteins*, Academic, New York, vol. 2, p. 255.

Wraith et al. (B). J. Gen. Virol 68: 433–440, 1987.

Dietzschold et al. Immunology 10(5):427–439, 1991.

Herzog et al. Virus Research 24: 77–89, 1992.

Perrin et al. Vaccine (United Kingdom) 9(8): 549–558, 1991.

Fu, Z.F. et al. PNAS (USA) 88: 200–2005, 1991.

Cubitt et al. J. Virol. 68 (3): 1371–1381, 1994.

Oberg et al. J. Virol 65(8): 4486–4489, 1991.

Castaneda et al., J. Virol. 64(1): 222–230,1990.

Wraith et al. (A) J. Gen. Virol. 66:1327–1331, 1985.

Piera et al. Int. J. Cancer 55: 148–152, 1993.

Fu, et al. 1991. Rabies virus nucleoprotein expressed in and purified . . . PNAS, USA. 88:2001–2005.

Dietzschold et al. 1987. Induction of protective immunity against . . . PNAS USA. 84:9165–9169.

*Primary Examiner*—Marianne P. Allen
*Assistant Examiner*—Mary K Zeman
*Attorney, Agent, or Firm*—Seidel, Gonda, Lavorgna & Monaco, PC

[57] ABSTRACT

Methods of enhancing an antigen-induced immune response through use of a ribonucleocapsid complex are provided. Composition containing a ribonucleocapsid complex and an antigen which are capable of enhancing the immune response to the antigen are also provided.

4 Claims, 6 Drawing Sheets

VIRAL RIBONUCLEOCAPSID AS AN IMMUNOLOGICAL ENHANCER

This is a continuation, of application Ser. No. 08/230,158, filed Apr. 19, 1994, abandoned.

BACKGROUND OF THE INVENTION

When delivered orally, most non-invasive and non-replicating antigens are not only poorly immunogenic but likely to induce an antigen-specific system hyporesponsiveness termed oral tolerance. The mechanism of oral tolerance is not fully understood but appears to be due to a deficit in systemic T cell help. Thus, despite the fact that oral vaccines are desirable for their ease of administration, few exist.

In rabies vaccination, however, both live-attenuated rabies and vaccinia-rabies glycoprotein recombinant virus delivered in edible bait have proven to be effective vaccines. Since rabies virus infection initiates from skin or muscle by a bite, it is clear that the ingested bait-vaccines induce a systemic immune response rather than a mucosal response and systemic tolerance which often accompanies the feeding of antigen. It has been proposed that the ability of the live vaccines to replicate is important in generating systemic immunity when administered orally. However, there is recent evidence to suggest that ingested killed rabies virus or rabies virus proteins also induce protective immunity.

Although virus neutralizing antibodies are invariably directed at the rabies glycoprotein, several previous studies have indicated that protective immunity to infection with rabies virus can be engendered by the intra-muscular administration of the rabies virus ribonucleocapsid. Dietzschold et al. (WO 8900861 A) disclose a method of inducing immunity to a rabies-related virus comprising administering a priming injection and one or more booster injections containing an antigen and a polypeptide having sequence homology with a rabies-related virus nucleoprotein. Antigenic determinants borne by the N protein of the rabies virus ribonucleocapsid have been proposed to play a role in the immunoprotective effect of this rabies vaccine.

Immunological enhancers, such as adjuvants, are substances which are added to vaccines or to antigens used for immunization to stimulate the immune response. Adjuvants cause an accumulation of mononuclear cells, especially macrophages, at the site of injection that is a granulomatous response. Macrophages involved in this first stage of the immune response take in the protein antigens and break them down into peptide fragments which are then exposed on the cell surface where they form a physical association with class II histocompatibility antigens. The T helper cells only recognize proteins associated with class II histocompatibility antigen, and not the free undegraded protein. The macrophages release monokines from the interleukin-1 family (IL-1) which stimulate the T helper cell to secrete IL-2. The actions of IL-1 and IL-2 result in the clonal expansion of T helper cells. The clonal expansion of T helper cells is followed by their interaction with B-cells, which in turn secrete antibody.

It has now been found that the nucleocapsid and ribonucleoprotein complex of a virus enhances the immune response in vivo to an antigen when administered in combination with the antigen. This enhanced immune response has been observed following various routes of administration including oral. The immunological enhancement by ribonucleocapsid complexes make them especially useful in development of effective oral vaccines.

SUMMARY OF THE INVENTION

An object of this invention is to provide a ribonucleocapsid complex which is capable of enhancing the immune response of a host to an antigen. These complexes can be provided to a host in a composition, either conjugated to or mixed with an antigen.

Another object of the invention is to provide a method of enhancing an antigen-induced immune response in a host by administering a composition comprising a ribonucleocapsid complex and an antigen.

BRIEF DESCRIPTION OF THE FIGURES

In FIG. 3A, the results of a KLH-specific ELISA of serum obtained after a single immunization are shown; FIG. 3B shows results after two immunizations. The values obtained with non-immune serum are shown by the dotted lines while third order linear regression analysis of the results of the immunized groups are represented by the solid and dashed lines.

FIG. 5A shows results of a radioimmunoassay for N-specific antibody of the IgG isotype. FIG. 5B shows results of a radioimmunoassay for IgA antibodies.

DETAILED DESCRIPTION OF THE INVENTION

Figure 1A:
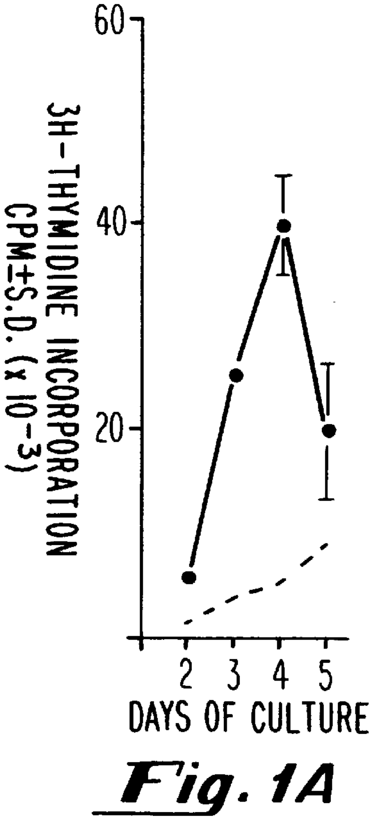
FIG. 1 shows T cell proliferative response to rabies virus following intra-muscular and per os administration of ribonucleocapsid complex. Mice received two doses ribonucleocapsid complex intra-muscular (5 μg; group A, FIG. 1A) or per os (50 μg; group B, FIG. 1B) ten and twenty days before assay or a single dose ten days prior to assay (intra-muscular group C, FIG. 1C; per os group D, FIG. 1D). Proliferation in the absence of added antigen (---) and in the presence of 10 μg/ml UV-inactivated rabies virus (●) was determined as described in materials and methods. The proliferation of non-immune cells is also shown (group E, FIG. 1E).
Figure 1B:
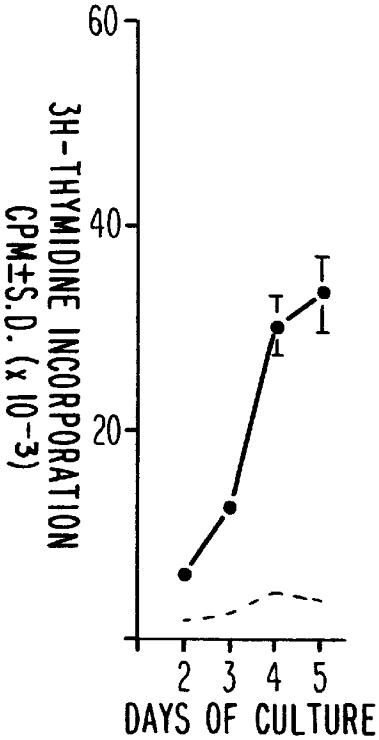
Figure 1C:
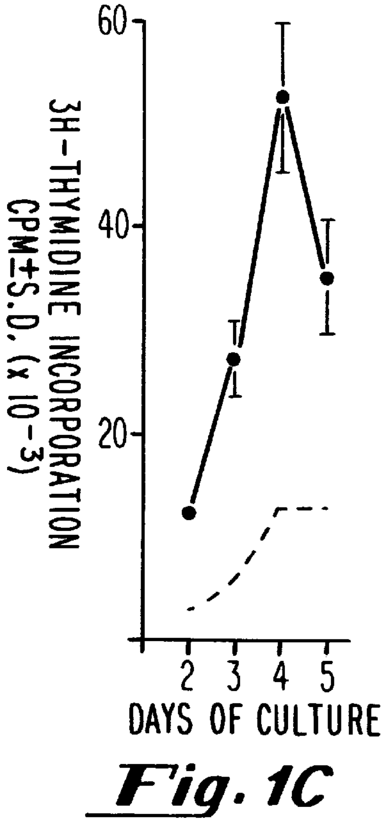
Figure 1D:
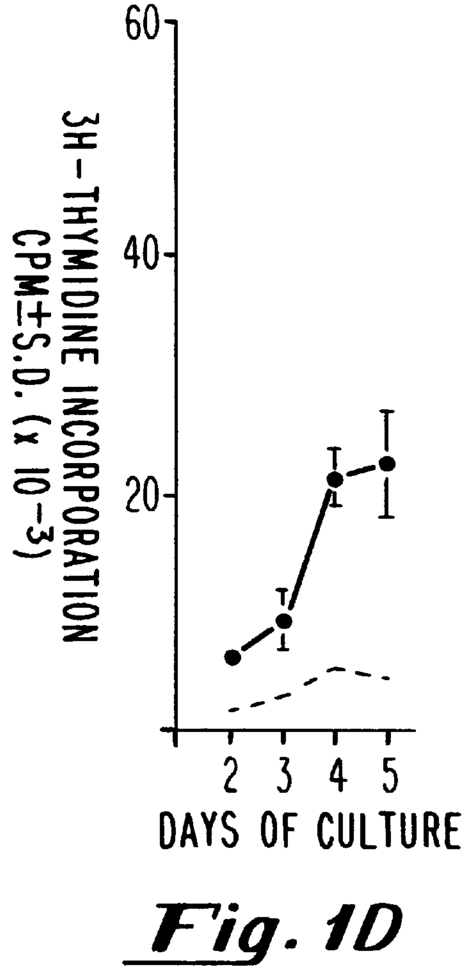
Figure 1E:
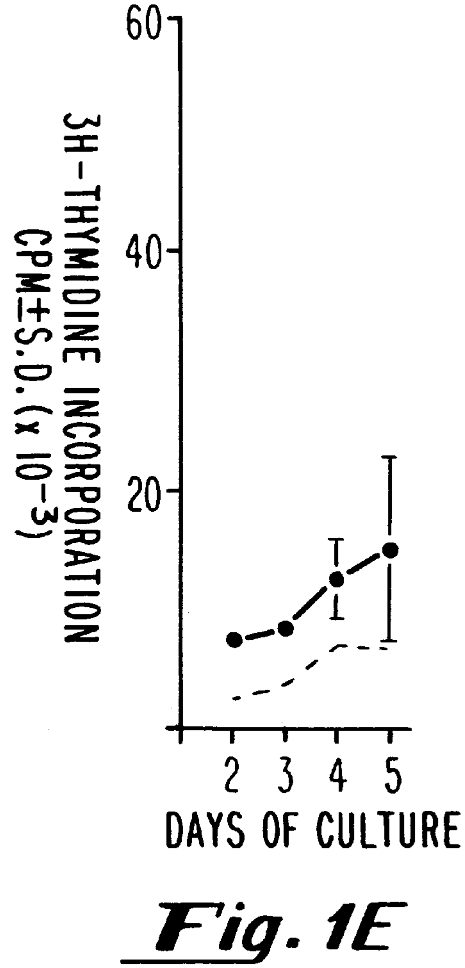

The present invention provides a ribonucleocapsid complex capable of enhancing antigen-induced immune stimulation. It has been found that a ribonucleocapsid complex, administered to a host in combination with an antigen enhances the immune response to the antigen. This enhanced immune response is observed following administration of antigens in association with a ribonucleocapsid complex. Administration to a host may be performed by any route, however, the enhanced immune response makes compositions comprising a ribonucleocapsid complex and antigen especially useful for oral or intranasal administration.

For purposes of this invention, the term "ribonucleocapsid complex" refers to the ribonucleocapsid and ribonucleoprotein deriving from a genome of a virus, preferably an RNA virus, more preferably a single stranded or negative stranded RNA virus, which has been purified from the virus or produced recombinantly. This term also encompasses the N-protein component of the ribonucleoprotein as well as other proteins which can also be used in combination with a selected antigen to produce an enhanced immune response. By "deriving from" it is meant that the ribonucleocapsid complex first originated from a selected virus, preferably a negative strand RNA virus, but may now be produced via recombinant or other bioengineering techniques. Examples of RNA viruses include, but are not limited to, members of the rhabdovirus, orthomyxovirus, paramyxovirus, picornavirus, coronavirus, arenavirus and retrovirus families. By "enhanced" or "enhancing" the immune response it is meant that the ribonucleocapsid complex is capable of boosting, heightening or intensifying the immune response to an antigen above and beyond the level of a conventional carrier for an antigen.

The ribonucleocapsid complex of the present invention, in combination with an antigen primes specific T cells and elicits antigen-specific antibodies. Enhanced production of both IgA and IgG type antibodies is observed. Cell mediated immunity is produced by T-cells or thymus-derived lymphocytes. T-cells are able to detect the presence of antigens through a system referred to as the T-cell antigen receptor. Upon detection of an antigen, T-cells direct the release of multiple T-cell lymphokines including members of the interleukin family such as IL-2, IL-4, and IL-5 as well as γ-IFN. For example, IL-2 is a T-cell growth factor which promotes the production of many more T-cells sensitive to the particular antigen. This production constitutes a clone of T-cells. The sensitized T-cells attach to cells containing the antigen. T-cells carry out a variety of regulatory and defense functions and play a central role in immunologic responses. When stimulated to produce a cell-mediated immune response, some T-cells respond by acting as killer cells, killing the host's own cells when these have become infected with virus and possibly when they become cancerous and therefore foreign. Some T-cells respond by stimulating B cells which make antibody molecules to differentiate and express their secreted gene product while other T-cells respond by suppressing immune responses.

Antibody or humoral immunity depends on the ability of B-cells, or bone marrow-derived lymphocytes, to recognize specific antigens. The mechanism by which B-cells recognize antigens and react to them is as follows. Each B cell has receptor sites for specific antigens on its surface. When an antigen attaches to the receptor site of a B-cell, the B-cell is stimulated to divide. The daughter cells become plasma cells which manufacture antibodies complementary to the attached antigen. Each plasma cell produces thousands of antibody molecules per minute which are released into the bloodstream. As the plasma cells die, others are produced, so that, once the body is exposed to a particular antigen, antibodies are produced against that antigen as long as the antigen is present in the body. Most B-cells appear to be regulated by the helper T-cells and suppressor T-cells. Helper T-cells appear to stimulate B-cells to produce antibodies against antigens, while suppressor T-cells inhibit antibody production by either preventing the B-cells from functioning or preventing the helper T-cells from stimulating the B-cells. Some B-cells, however, are T-cell independent and require no stimulation by the T-cells.

The ribonucleocapsid complex of the present invention and derivatives thereof can act either as carriers of other antigens or enhancers of the activity of cells of the immune system to boost immunity to the associated antigens. By "associated" it is meant that antigens from any source can be mixed, chemically coupled, physically joined, incorporated into, or attracted by charge, or in any way delivered at the same site within a reasonable amount of time with the ribonucleocapsid complex. By a "reasonable amount of time" it is meant that the ribonucleocapsid complex and antigen can be administered hours to as long as days apart if they are administered to the same site. The term "carrier" refers to a molecule, carrying other antigenic determinants, which can enhance the immune response and stimulate antibody production to the antigenic determinants. While there are many conventional carriers well known to those of skill in the art, the ribonucleocapsid complex of the present invention is capable of stimulating the immune response to associated antigenic determinants to a much greater extent than the conventional carrier without the need for chemical association.

Figure 5A:
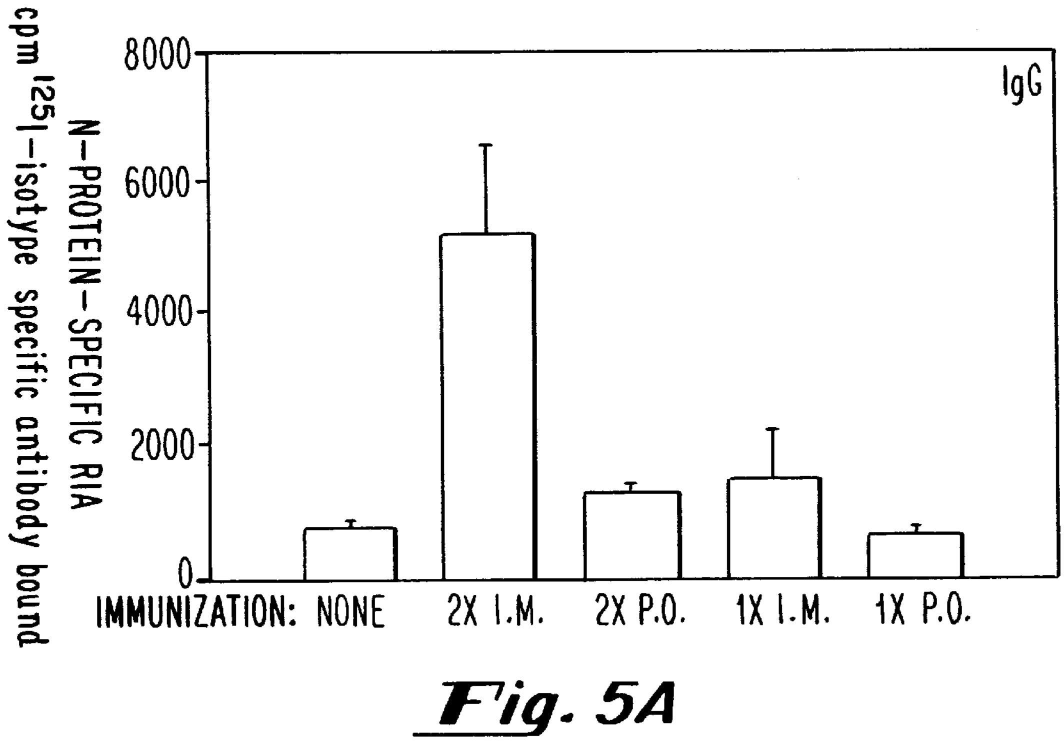
FIGS. 5A and 5B show antibody response to rabies N-protein following immunization with the ribonucleocapsid complex orally and intramuscularly. Serum samples were obtained from mice immunized either 1 time i.m. or p.o. or two times i.m. or p.o.
Figure 5B:
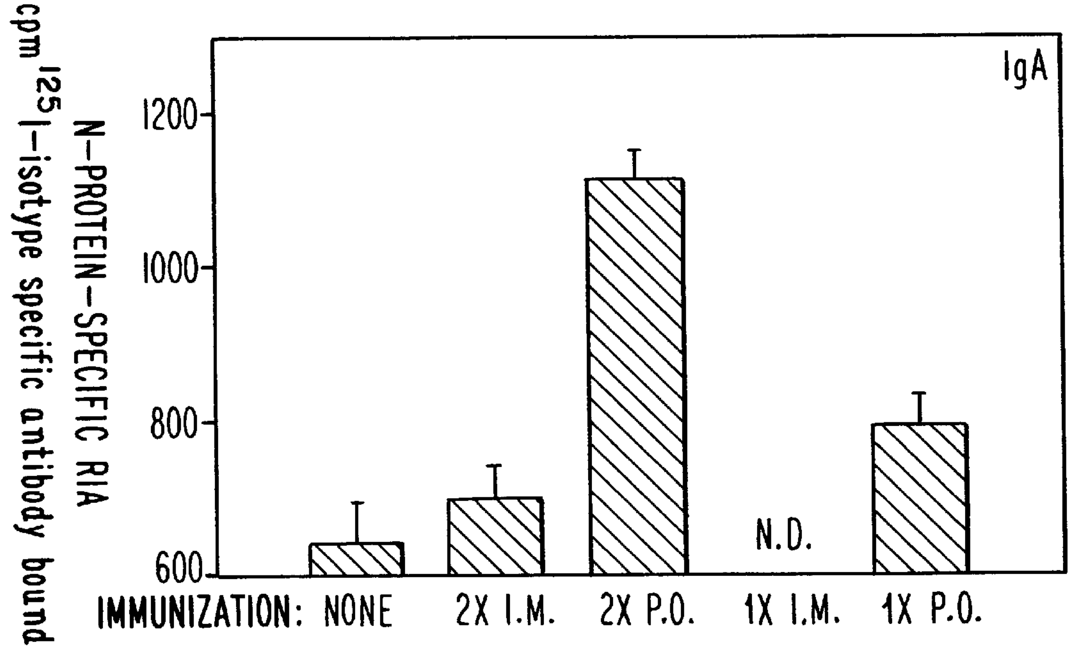

The ability to enhance the immune response gives the ribonucleocapsid complex wide application in enhancing the responses of current vaccines as well as conferring immunogenicity on antigens which are poor stimulators of immunity on their own. Thus, the ribonucleocapsid complex can be used to make any antigen more effective. Accordingly, this complex is useful in enhancing a response to vaccines, as well as to help induce responses to cancers and stimulate responses to local infections by administration of the ribonucleocapsid complex at the disease site or in association with antigens from a material or agent which it is desired to stimulate a response to. Since oral administration of the ribonucleocapsid complex has been shown to be effective and IgA production has been detected, the ribonucleocapsid complex can also be used to stimulate a mucosal immune response to antigens for the development of mucosal vaccines (see FIG. 5B).

The present invention also provides methods of enhancing an antigen-induced immune response in a host comprising administering to a host an effective amount of a composition comprising a ribonucleocapsid complex and an antigen so that a immune response to said antigen is enhanced. Such compositions can be administered to the host by any route, however, oral and intranasal administration is preferred. The ribonucleocapsid complex may be conjugated with the antigen or the two components may be administered as a mixture at the same time. The term "effective amount" refers to an amount of the composition which when administered invokes an enhanced immune response in a host. Such amounts may be determined by routine experimentation by those of skill in the art upon this disclosure.

Oral immunization with ribonucleocapsid complex in mice elicited systemic proliferative T cells capable of responding to rabies virus in vitro (See FIGS. 1A through 1E). Ribonucleocapsid complex derived from a rabies virus was administered either intramuscularly or orally in a single does or in two doses with a ten day interval. T cells isolated from the spleens of these immunized mice were found to proliferate in vitro in the presence of rabies virus regardless of the route of immunization indicating that T cells had been primed in the immunized mice. The proliferative response to T cells from orally primed animals was slightly lower and developed more slowly than that of mice immunized intra-muscularly. However, the T cell response to the rabies ribonucleocapsid complex was significantly enhanced when orally immunized mice where given a second dose of antigen via the same route. Intra-peritoneal administration of the rabies ribonucleocapsid complex also resulted in proliferation of T cells upon exposure to the rabies virus.

Figure 2:
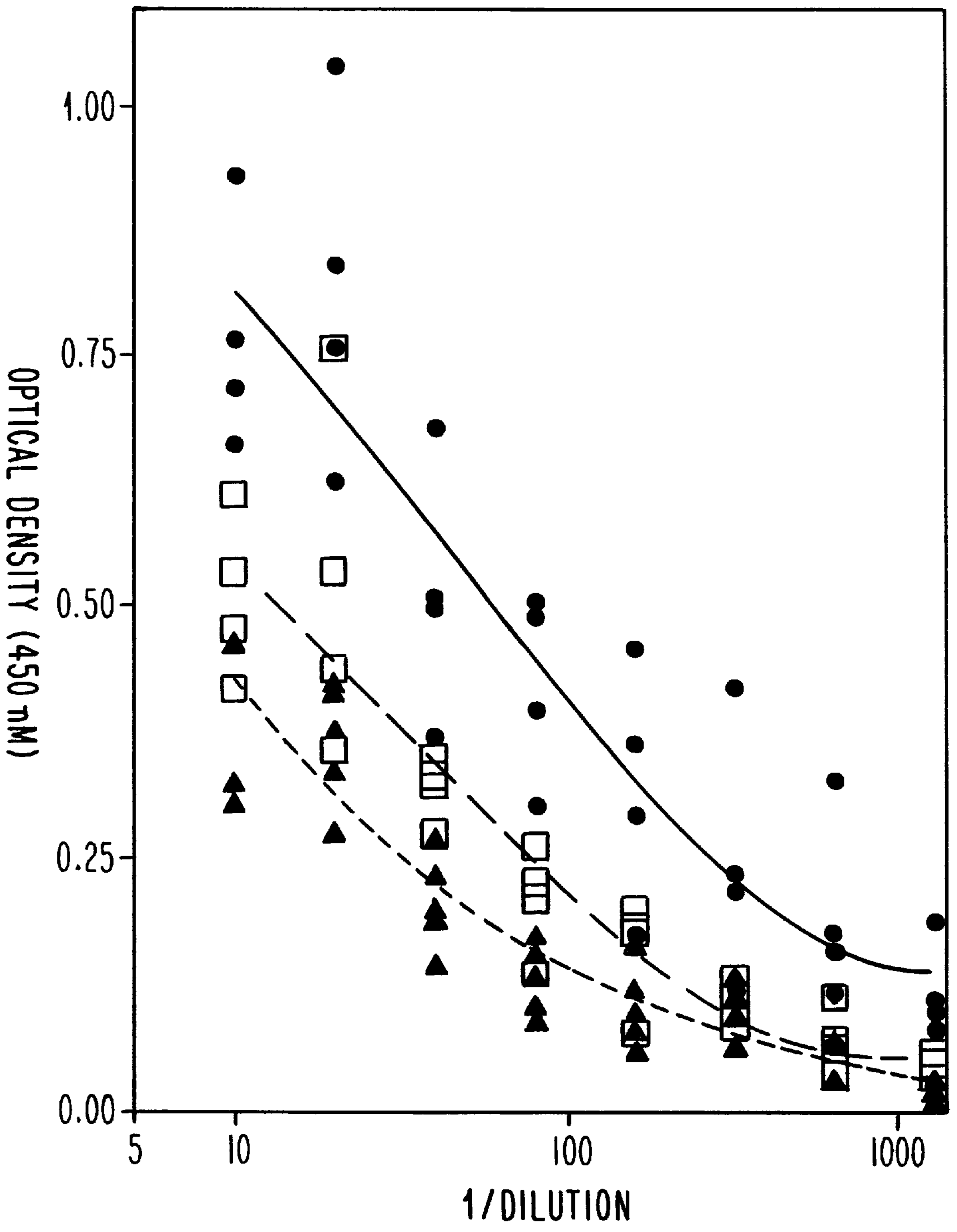
FIG. 2 is a comparison of the antibody response to intra-muscular immunization with ribonucleocapsid complex-HSV peptide conjugate versus a mix of ribonucleocapsid complex plus HSV-peptide. Groups of 4 mice were immunized twice intra-muscular with HSV-peptide alone (▲, short dashed line), ribonucleocapsid complex-HSV peptide conjugate (□, long dashed line), or a mix of ribonucleocapsid complex plus the peptide (•, solid line). The results of an ELISA for peptide specific antibody are shown. The lines depict a third order linear regression analysis of the results of each group.
Figure 3A:
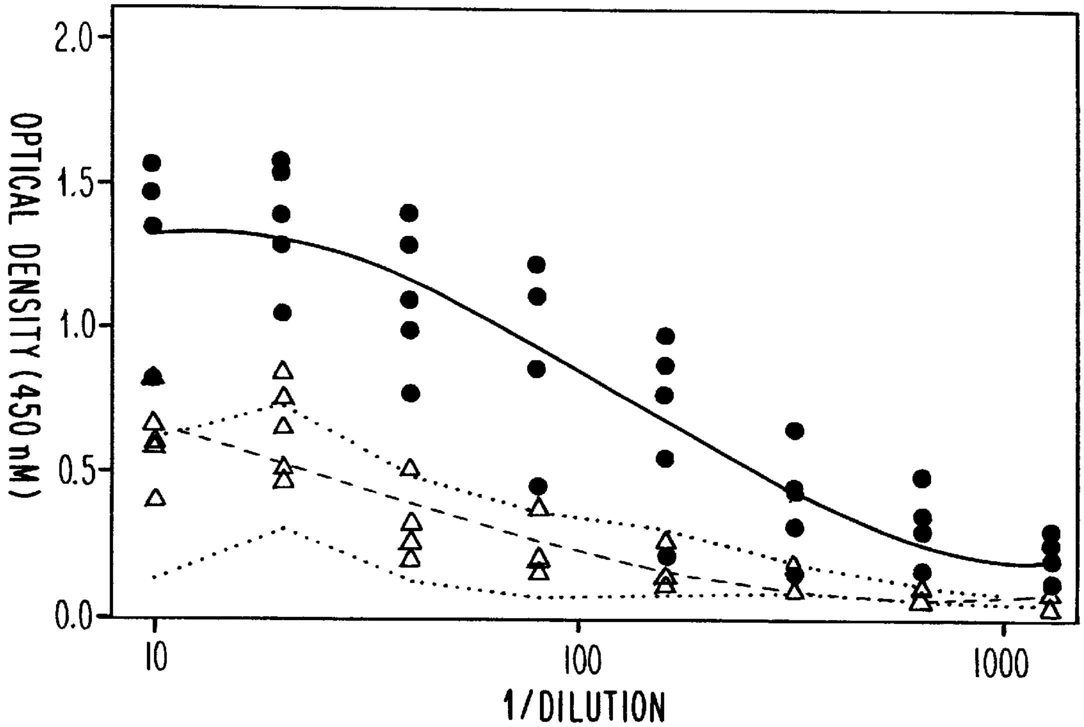
FIGS. 3A and 3B show the effect of ribonucleocapsid complex on the humoral response to KLH. Groups of 5 mice were immunized intra-muscular with KLH (Δ, dashed line) or a mixture of KLH plus ribonucleocapsid complex (•, solid line).
Figure 3B:
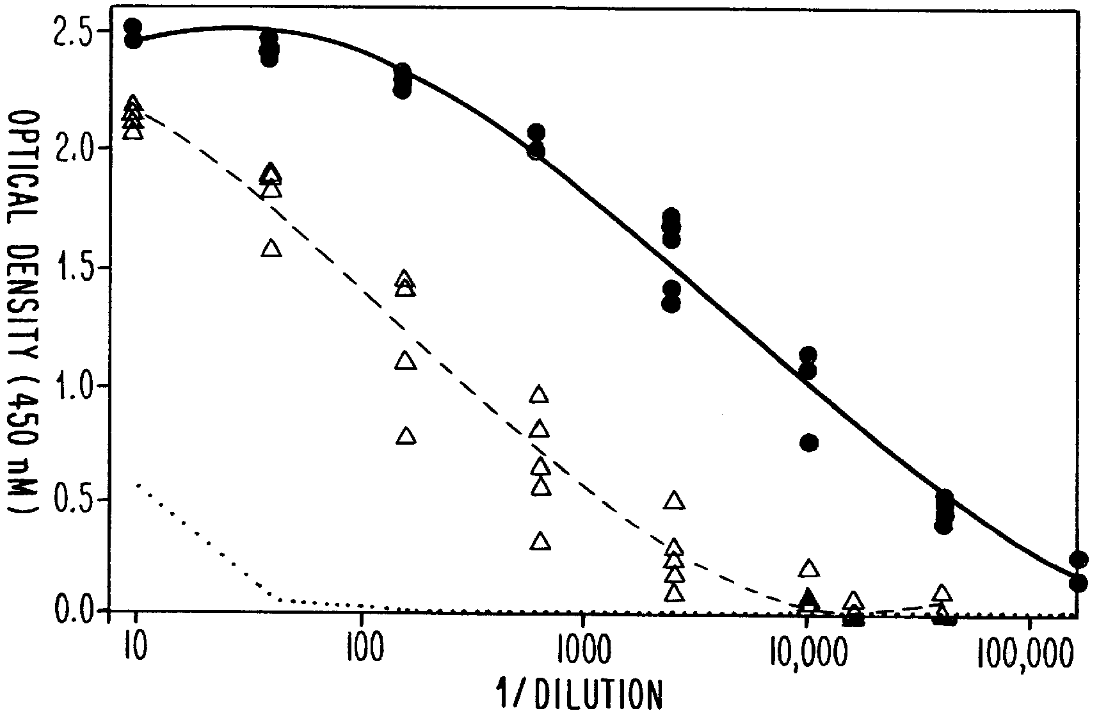
Figure 4:
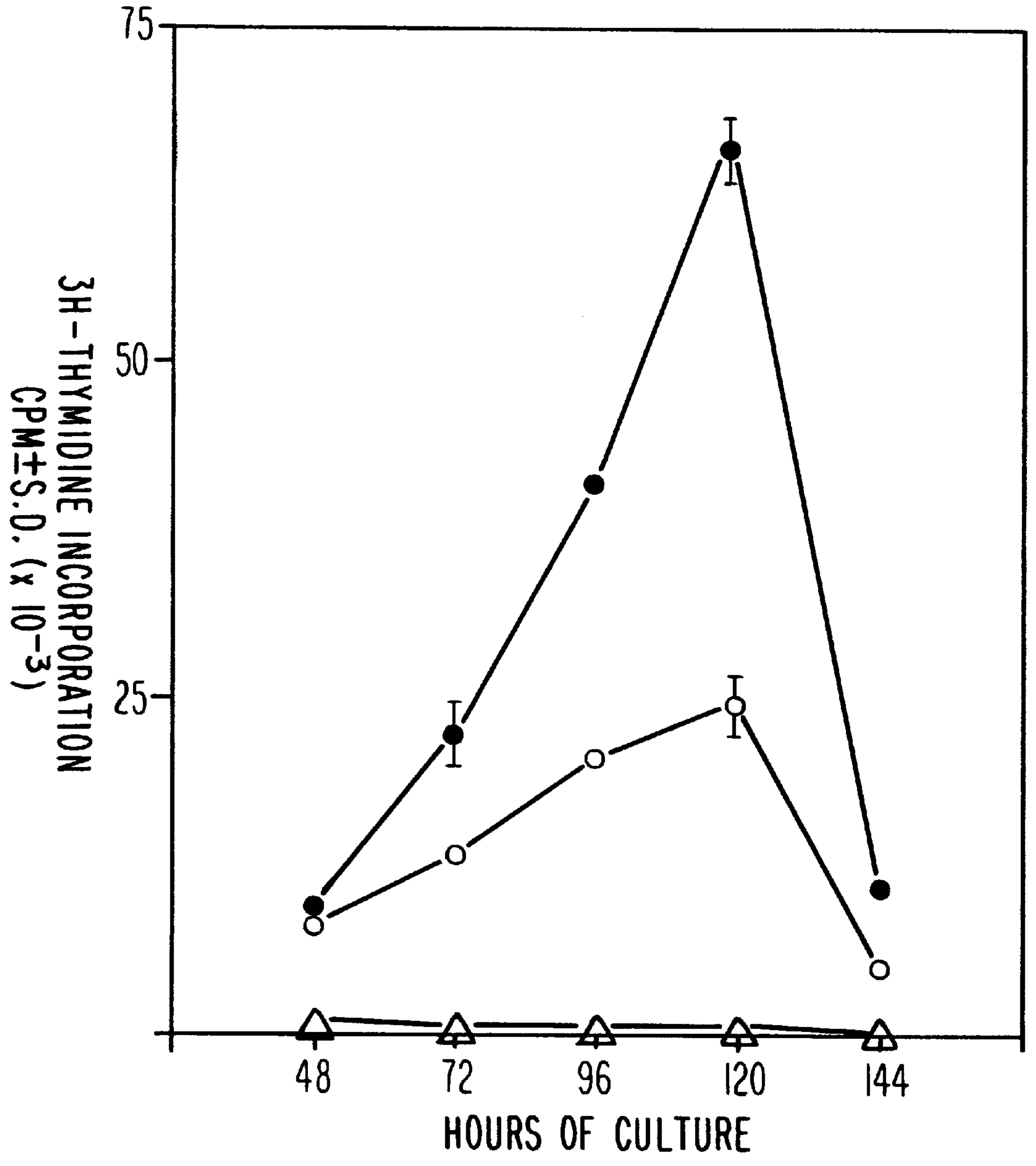
FIG. 4 shows the effect of the ribonucleocapsid complex on the T cell proliferative response to KLH. T cells were isolated from the pooled spleens of mice immunized twice i.m. with KLH (○), a mixture of ribonucleocapsid plus KLH (●), or untreated (▽). The T cells were cultured with irradiated autologous spleen cells and KLH (10 μg/ml). Proliferation was measured by $^3$H-thymidine incorporation at 48, 72, 96, 120 and 144 hours.

To distinguish between antigen specific and non-specific effects, the ability of a ribonucleocapsid complex derived from rabies virus to function as a carrier for other antigenic determinants by coupling it to an HSV-derived peptide and compared the immunogenicity of this conjugate with that of a mix of the two components was examined. Immunization with the ribonucleocapsid complex-peptide conjugate promoted a higher level of serum anti-peptide antibody than administration of the peptide alone, which did not significantly differ from immunization with ribonucleocapsid complex only or no treatment (see FIG. 2). The highest titers of anti-peptide antibody were seen in mice that had received a mix of ribonucleocapsid complex plus the peptide. Further experiments have demonstrated that ribonucleocapsid complex can also enhance humoral immune responses to a variety of more complex antigens. FIG. 3 shows the results of a comparison of intra-muscular immunization with KLH alone versus a mix of KLH plus ribonucleocapsid complex. A single dose of a mix of KLH plus ribonucleocapsid complex was sufficient to induce strong antibody responses to KLH in 4 of the 5 mice tested while the serum anti-KLH titers seen following administration of KLH alone were not significantly greater than the higher of the two non-immune controls (see FIG. 3A). A second immunization with the same reagents boosted the anti-KLH response in both KLH alone and KLH plus ribonucleocapsid complex groups although a large difference in the mean titers was maintained (see FIG. 3B). In this case, the inclusion of ribonucleocapsid complex in primary and booster immunizations was responsible for an approximately 100 fold difference in the mean serum anti-KLH titers. Moreover, the variations in the titers seen in different mice was minimized in the ribonucleocapsid complex plus KLH group. An admixture of an antigen and the ribonucleocapsid complex was also shown to enhance the T cell proliferative response to the antigen (see FIG. 4). T cells isolated from mice immunized twice with a mixture of ribonucleocapsid complex plus KLH had a much higher proliferative response than T cells isolated from mice immunized twice with only KLH. Administration of the ribonucleocapsid complex plus KLH orally was also shown to significantly stimulate IgA antibody production when compared to intramuscular administration indicating that a mucosal immune response is also produced by the complex (see FIGS. 5A and 5B). Accordingly, the ribonucleocapsid complex can be used in the development of mucosal vaccines also.

The following examples are provided for illustrative purposes only and are not intended to limit the invention.

EXAMPLES

Example 1 Viruses and Antigens

The fixed rabies strains ERA and CVS-11 were propagated on BHK-21 cells monolayers and purified in accordance with the methods described in Wiktor, T. J., et al. *J. Virol.* (1977) 21:626–635 and Schneider et al., *J. Virol.* (1973) 11:748–755. The purified virus was suspended in phosphate-buffered saline, inactivated with β-propiolactone and adjusted to a protein concentration of 100 μg/ml. Viral ribonucleocapsid complex was isolated from rabies virus-infected BHK-21 cells and rabies N protein was purified from insect cells infected with a recombinant baculovirus expressing rabies N protein as described in Fu, Z. F., et al. *Proc. Natl. Acad. Sci. USA* (1991) 88:2001–2005. Keyhole limpet hemocyanin was purchased from the Sigma Chemical Company (St. Louis, Mo.) and used as the conventional test antigen. HSV-2 peptide was synthesized using Merrifield solid phase methods as described in Erickson, B. W. and Merrifield, R. B. (1976) In: Neurath, H., Hill, R. L. (eds) *The Proteins*, vol. 2, Academic, New York, p. 255.

Example 2 Determination of anti-N, anti-KLH and anti-HSV-2 peptide antibodies

Radioimmunoassay (RIA) for N-protein-specific antibody as well as enzyme-linked immunoabsorbant assay (ELISA) for HSV-2 specific and KLH-specific antibody were performed by conventional means using polystyrene plates (Dynatech, Immunolon 4) coated with baculovirus-expressed rabies N protein, HSV-2-KLH conjugate, and KLH respectively. Following incubation with test sera, antibody specifically bound to the plates was detected using specific anti-mouse Ig reagents. For RIA, $^{125}$I-labelled rabbit anti-mouse IgG (heavy chain-specific, mixed γ1, γ2a, and γ2b) or rabbit anti-mouse IgA (α heavy chain specific) were used. Peroxidase-conjugated goat anti-mouse IgG (whole molecule, Sigma No. A-4416) was employed in an ELISA with 3,3',5,5'-tetramethyl benzidine dihydrochloride as substrate. The color change following the addition of $H_2SO_4$ to stop the reaction after 30 minutes was measured at 450 nm in a Bio-kinetics reader (Bio-Tek Instruments, Inc., Winooski, Vt.).

Example 3 Priming of mice for VNA with ribonucleocapsid complex

Six to eight week old female C3H/HeJ mice were obtained from the Jackson Laboratory (Bar Harbor, Me.). Six week mice were immunized intra-peritoneal, intra-muscular, or intradermal with 0.4, 2, and 10 μg of ribonucleocapsid complex. Mice were immunized orally with 50 μg ribonucleocapsid complex with and without 10 μg cholera toxin B subunit. Oral immunization was carried out by placing 50 μl of antigen diluted in phosphate buffered saline in the oral cavity. Two weeks after priming, groups of 10 mice primed with either ribonucleocapsid complex or phosphate buffered saline were immunized intra-peritoneal with 5 μg of inactivated Evelyn-Rokitnicki-Abelseth (ERA) strain of rabies virus (ERA-BPL). Blood was collected 10, 45, and 158 days after booster immunization.

Example 4 Stimulation of rabies virus-specific T cells

For the stimulation of rabies virus-specific T cells, six week old female mice were immunized with 5 μg ribonucleocapsid complex intra-muscular, 20 μg ribonucleocapsid complex orally, or 20 μg N-protein orally either a single time or twice with an interval of ten days. The mice were sacrificed and antigenspecific splenic T cell proliferation assessed at least 10 days after immunization.

Example 5 Cell culture and antigen-specific proliferative assay

Cells were prepared and cultured as described. Single cell suspensions were prepared from aseptically removed spleens by teasing through stainless steel mesh in phosphate buffered saline. Red cells were lysed by hypotonic shock and T cells were isolated by panning on goat anti-mouse Ig coated plates. T cells (250,000) from various groups of mice were cultured with unselected spleen cells (100,000 to 200,000) from non-immune mice as a source of antigen-presenting cells in 200 μl volumes in round bottom microtitre plates in the presence of the antigens indicated in the figure legends. The medium employed was the alpha-modification of MEM (Gibco) supplemented with 4 mM L-glutamine (Gibco), $5\times10^{-5}$M 2-ME (Sigma), 25 mM HEPES, gentamycin, and 0.6% fresh mouse serum. At the indicated times, cultures were pulsed with 1 $\mu$Ci of methyl-$^3$H-thymidine (Specific activity 65 Ci/mmole; ICN Radiochemicals) for 4 hours. The cultures were then harvested using a multiple sample harvester (Skatron) and the water insoluble radioactivity counted on an LKB rack beta (LKB-Wallac) using conventional liquid scintillation techniques.

Example 6 Effect of ribonucleocapsid complex on the humoral response to heterologous antigens HSV-2 peptide alone, ribonucleocapsid complex-HSV-2 peptide conjugate, or a mix of ribonucleocapsid complex with HSV-2 peptide or KLH were administered intramuscular (5 $\mu$g ribonucleocapsid complex plus 20 $\mu$g peptide or KLH, 20 $\mu$g peptide alone, 20 $\mu$g conjugate) to groups of mice twice with an interval of approximately ten days. Serum was obtained both prior to and 10 to 14 days following the second immunization.

What is claimed is:

1. A method of enhancing an antigen-induced immune response in a host comprising administering to a host an effective amount of an isolated ribonucleocapsid complex containing a ribonucleocapsid and a ribonucleoprotein derived from an RNA virus selected from the group consisting of rhabdovirus, orthomyxovirus, paramyxovirus, picornavirus, coronavirus, arenavirus and retrovirus and an antigen containing other determinants not present in the RNA virus from which the ribonucleocapsid complex is derived so that an immune response to said other determinants is enhanced.

2. The method of claim 1 wherein the antigen is conjugated to the ribonucleocapsid complex.

3. The method of claim 1 wherein the composition is administered orally or intranasally.

4. A composition capable of inducing an antigen-induced immune response consisting essentially of an antigen and an isolated ribonucleocapsid complex containing a ribonucleocapsid and a ribonucleoprotein derived from an RNA virus selected from the group consisting of rhabdovirus, orthomyxovirus, paramyxovirus, picornavirus, coronavirus, arenavirus and retrovirus, wherein said antigen contains other determinants not present in the RNA virus from which the ribonucleocapsid complex is derived, and wherein the composition is capable of inducing an immune response to said other determinants.

* * * * *